(12) United States Patent
Okazoe et al.

(10) Patent No.: US 7,314,952 B2
(45) Date of Patent: Jan. 1, 2008

(54) FLUORINATED ADAMANTANE DERIVATIVES

(75) Inventors: Takashi Okazoe, Yokohama (JP); Kunio Watanabe, Yokohama (JP); Masahiro Ito, Yokohama (JP); Eisuke Murotani, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 91 days.

(21) Appl. No.: 11/143,978

(22) Filed: Jun. 3, 2005

(65) Prior Publication Data

US 2005/0277785 A1 Dec. 15, 2005

Related U.S. Application Data

(63) Continuation of application No. PCT/JP03/15879, filed on Dec. 11, 2003.

(30) Foreign Application Priority Data

Dec. 11, 2002 (JP) .............................. 2002-359471

(51) Int. Cl.
*C07C 69/63* (2006.01)
(52) U.S. Cl. ..................................... 560/227
(58) Field of Classification Search ................ 560/227
See application file for complete search history.

(56) References Cited

U.S. PATENT DOCUMENTS

| 4,284,558 | A | 8/1981 | Barton et al. |
| 7,084,295 | B2 | 8/2006 | Tanaka et al. |
| 2005/0277785 | A1 | 12/2005 | Okazoe et al. |

FOREIGN PATENT DOCUMENTS

| CA | 1064475 | 10/1979 |
| EP | 1 460 057 | 9/2004 |
| JP | 51-4102 | 1/1976 |
| JP | 57-79187 | 5/1982 |
| JP | 4-502319 | 4/1992 |
| JP | 9-43848 | 2/1997 |
| JP | 2001-60583 | 3/2001 |
| JP | 2003-280205 | 10/2003 |
| JP | 2004-123687 | 4/2004 |
| JP | 2005-23066 | 1/2005 |
| JP | 2005-89363 | 4/2005 |
| WO | WO 00/56694 | 9/2000 |
| WO | WO 03/055841 | 7/2003 |
| WO | WO 2004/050725 | 6/2004 |
| WO | WO 2004-052832 A1 | 6/2004 |

OTHER PUBLICATIONS

J.L.Adcock, H.Luo, and S.S.Zuberi Aerosol Flurination of 1-Chloroadamantane, 2-Chloroadamantane, and Methyl 1-Adamantylacetate: A Novel Synthetic Approach to 1- and 2-Substituted Hydroxyl-, Methyl-, and (Difluoromethyl)-F-adamantanes J.Org.Chem. 4749-4752, 57, 1992.*

Färcasiu et al, J. Am. Chem. Soc., 1985, vol. 107, pp. 5717-5722.
Adcock et al, J. Org. Chem., 1996, vol. 61, pp. 5073-5076.
Adcock et al, J. Org. Chem., 1995, vol. 60, pp. 1099-2002.
Adcock et al, J. Org. Chem., 1995, vol. 57, pp. 4297-4300.
Helmut Duddeck, et al., "Synthesen und $^{13}$C-NMR-spektroskopische Untersuchungen trifluormethylsubstituierter Adamantane", Liebigs Ann. Chem., No. 3, 1985, pp. 545-554 (with English Abstract).
Douglas J. Raber, et al. "Structure Elucidation with Lanthanide-Induced Shifts 5. Evaluation of the Binding Ability of Various Functional Groups 1"; Monatshefte fur Chemi vol. 111, 43-52 (1980).
Database CA (Online); Chemical Abstracts Service, Columbus, Ohio, US; Kunihiko Kodama, et al. "Positive-working light-sensitive resist composition containing alkali-sensitive compound" XP002380188 and JP 2001 109156 A2 (Fuji Photo Film Co., Ltd., Japan) Apr. 20, 2001.

(Continued)

*Primary Examiner*—Yvonne Eyler
*Assistant Examiner*—Sudhakar Katakam
(74) *Attorney, Agent, or Firm*—Oblon, Spivak, McClelland, Maier & Neustadt, P.C.

(57) ABSTRACT

The present invention provides novel compounds which are useful for the production of fluorinated adamantane derivatives excellent in etching resistance and useful as photolithographic material and so on. Namely, the present invention provides compounds represented by the following formulae (3) and (4):

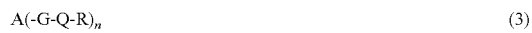

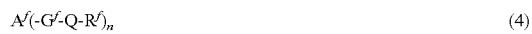

provided that the symbols in the formula have the following meanings:

A: a n-valent group having n hydrogen atoms of adamantane converted to connecting bonds, wherein hydrogen atoms not converted to connecting bonds, may be each substituted by an alkyl group, R: a fluorinated monovalent organic group, n: an integer of from 1 to 4, G: —$CH_2$— or a single bond, Q: —COO— or —OCO—, $A^f$: a n-valent group (A) having n hydrogen atoms bonded to carbon atoms of adamantane converted to connecting bonds, wherein hydrogen atoms not converted to connecting bonds, may be each substituted by an alkyl group, in which at least one of hydrogen atoms forming C—H bonds is substituted by a fluorine atom, $R^f$: a fluorinated monovalent organic group, $G^f$: —$CF_2$— or a single bond.

11 Claims, No Drawings

OTHER PUBLICATIONS

T. William Bentley, et al. "Weakly Nucleophilic Leaving Groups. Solvolyses of 1-Adamantyl and t-Butyl Heptafluorobutyrates and Trifluoracetates"; J. Chem. Soc. Perkin Trans. vol. ii (1989).

Database CA (Online); Chemical Abstracts Service, Columbus, Ohio, US; V.A. Soloshonok, et al. "Reaction fo 3,7-dimethylenebicyclo (3.3.1) nonane with pyridinium perfluorocarboxylates"; XP 002380189 and Database accession No. 1990:405759 abstract and Zhurnal Organicheskoi Khimii , 25(10), 2242-3 Coden; Zorkae; ISSN: 0514-7492, 1989.

Database CA (Online); Chemical Abstracts Service, Columbus, Ohio, US; D.T. Stoelting, et al, "Solvolysis of 1-(3-noradamantyl)-2-methylpropyl and 1-(3-noradamantyl)-2,2-dimethylpropyl pentamethylbenzenesulfonates" XP002380190 Database accession No. 1993: 147003 and Croatica Chemica Acta, 65(3) 517-38 Coden: CCACAA; ISSN: 001-1643, 1992.

Pavel A. Krasutsky, et al. "Observation of a Stable Carbocation in a Consecutive Criegee Rearrangement With Trifluoroperacetic Acid" J. Org. Chem. vol. 65, pp. 3926-3933, 2000.

Stephen R. Jones, et al. "Mechanism of Oxidation of Saturated Hydrocarbons by Lead(iv), Cobalt(iii), and Manganese(iii) Trifluoroacetates" J.C.S. Chem. Comm. 1976.

Pavel A. Krasutsky, et al. "Heterolytic decarboxylation involving acyltrifluoroacetyl peroxide intermediates" Tetrahedron Letter 43(48), pp. 8687-8691.

James L. Adcock, et al. Aerosol fluorination of 1-Chloroadamantane, 2-Chloroadamantane, 2-Chloroadamantane, and Methyl 1-Adamantylacetate: A Noval Synthetic Approach to 1-and 2-Substituted Hydryl-, Methyl-, and (Difluoromethyl)- F-Adamantanes; Journal of Organic Chemistry, 57(17), pp. 4749-4752, 1992.

James L. Adcock, et al. "Polarized C-H Groups as Novel Hydrotgen-Bond Donors in Hydryl-F-alkyl Esters: Unequivocal Examples fo rthe Pinchas Effect" Journal of Organic Chemistry, 60(7), pp. 1999-2002 (1995).

Oldrich Paleta, et al. "Synthesis of 1-Adamantanol 2,3,3-Trifluoroacrylate" Journal of Fluorine chemistry 47(3) pp. 435-440, (1990).

Klaus Banert, et al. "Nucleophile Substitution bei 4,4-Dimethyl-2-adamantyl- Substraten: Ruckseitenangriff bei 2-Adamantan-Derivaten" Chemische Berichte, vol. 119(12), pp. 3826-3841, (1986).

Neil A. Marron, et al. "A Direct Photochemical Synthesis of 1,2-Disubstituted Adamantanes" Synthetic Communications, vol. 7(8), pp. 515-520 (1977).

Muthiah Manoharan, et al., "Lipidic Nucleic Acids" Tetrahedron Letters, vol. 36, No. 21, 1995, pp. 3651-3654.

U.S. Appl. No. 11/611,183, filed Dec. 15, 2006, Oharu et al.

U.S. Appl. No. 11/567,391, filed Dec. 6, 2006, Wang et al.

* cited by examiner

FLUORINATED ADAMANTANE DERIVATIVES

TECHNICAL FIELD

The present invention relates to novel fluorinated adamantane derivatives and further to novel intermediates useful for the production of such derivatives.

BACKGROUND ART

Non-fluorinated adamantane derivatives are useful as compounds to constitute etching resistant thin film materials for protecting substrate layers in an etching process employing photolithography (JP-A-2001-60583).

For high densification in order to meet an increase in the amount of information, photolithography employing a laser beam with a shorter wavelength is adopted. However, with conventional adamantane derivatives, the transmittance to such a laser beam has been inadequate.

DISCLOSURE OF THE INVENTION

The present inventors have considered that fluorinated adamantane derivatives may possibly be materials which are excellent in transmittance of light and excellent in etching resistance and which can be applied to finner photolithography and have arrived at the present invention. Namely, it is an object of the present invention to provide novel fluorinated adamantane derivatives which can be provided by an economically advantageous method from readily available materials.

The present inventors have found it possible to produce a compound having a fluorinated adamantane skeleton and having reactive groups such as a —OH group, a —COF group, a keto group, etc. (i.e. a fluorinated adamantane derivative of the present invention) by using a readily available compound having an adamantane skeleton and by subjecting it to fluorination and a chemical conversion by certain specific methods. This fluorinated adamantane derivative is a useful compound which can further be led to various useful compounds by conversions utilizing the reactivities of the —OH group, the —COF group, etc. The compounds derived from the fluorinated adamantane derivative can be etching resistant thin film materials which can be materials excellent in both etching resistance and transmittance to light in the photolithography employing a laser beam with a short wavelength.

Namely, the present invention provides an invention having the following constructions:

1. A compound represented by the following formula (3)

  (3)

provided that the symbols in the formula have the following meanings:
   A: a n-valent group having n hydrogen atoms of adamantane converted to connecting bonds, wherein hydrogen atoms not converted to connecting bonds, may be each substituted by an alkyl group,
   R: a fluorinated monovalent organic group,
   n: an integer of from 1 to 4,
   G: —$CH_2$— or a single bond,
   Q: —COO— or —OCO—.

2. The compound according to 1, wherein Q is —COO—.
3. A compound selected from compounds represented by the following formulae (wherein R is a fluorinated monovalent organic group):

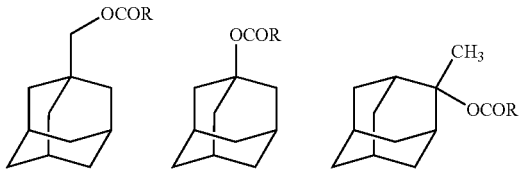

4. The compound according to 1, 2 or 3, wherein R is a $C_{2-20}$ fluorinated alkyl group or a $C_{2-20}$ fluorinated alkyl group containing an etheric oxygen atom.
5. The compound according to 1, 2 or 3, wherein R is a $C_{2-20}$ perfluoroalkyl group or a $C_{2-20}$ perfluoroalkyl group containing an etheric oxygen atom.
6. The compound according to 1, 2 or 3, wherein R is —$CF(CF_3)OCF_2CF_2CF_3$.
7. A compound represented by the following formula (4)

  (4)

provided that the symbols in the formula have the following meanings:
   $A^f$: a n-valent group (A) having n hydrogen atoms bonded to carbon atoms of adamantane converted to connecting bonds, wherein hydrogen atoms not converted to connecting bonds, may be each substituted by an alkyl group, in which at least one of hydrogen atoms forming C—H bonds is substituted by a fluorine atom,
   $R^f$: a fluorinated monovalent organic group,
   n: an integer of from 1 to 4,
   $G^f$: —$CF_2$— or a single bond,
   Q: —COO— or —OCO—.

8. The compound according to 7, wherein Q is —COO—.
9. A compound selected from compounds represented by the following formulae (wherein $R^f$ is a fluorinated monovalent organic group):

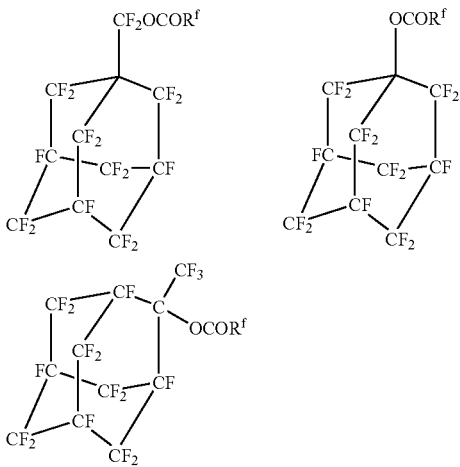

10. The compound according to 7, 8 or 9, wherein $R^f$ is a $C_{2-20}$ perfluoroalkyl group or a $C_{2-20}$ perfluoroalkyl group containing an etheric oxygen atom.

11. The compound according to 7, 8 or 9, wherein $R^f$ is —$CF(CF_3)OCF_2CF_3$.

12. A compound represented by the following formula:

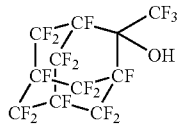

(5c)

BEST MODE FOR CARRYING OUT THE INVENTION

In this specification, the monovalent organic group means a monovalent group essentially containing carbon atom(s). The monovalent organic group may, for example, be an organic group having C—H portions, or an organic group having carbon-carbon unsaturated bonds, and is preferably a monovalent organic group having C—H portions. The monovalent organic group having C—H portions may, for example, be a monovalent saturated hydrocarbon group, a monovalent saturated hydrocarbon group containing an etheric oxygen atom, a partially halogenated monovalent saturated hydrocarbon group, or a partially halogenated monovalent saturated hydrocarbon group containing an etheric oxygen atom. Here, the etheric oxygen atom means an oxygen atom constituting an ether bond (C—O—C). The monovalent organic group is preferably a monovalent saturated organic group wherein carbon-carbon bonds are composed of single bonds only, or a monovalent saturated hydrocarbon group containing an etheric oxygen atom. The monovalent saturated hydrocarbon group may, for example, be an alkyl group, a cycloalkyl group or a monovalent saturated hydrocarbon group having a cyclic structure (such as a cycloalkyl group, a cycloalkylalkyl group or a group having such a group as a partial structure) and is preferably an alkyl group.

The monovalent saturated hydrocarbon group containing an etheric oxygen atom, may, for example, be an alkyl group having an etheric oxygen atom inserted between carbon-carbon atoms, or a cycloalkyl group having an etheric oxygen atom inserted between carbon-carbon atoms.

In this specification, "fluorinated" means that some or all of portions which may be fluorinated, in a group to be fluorinated, are fluorinated. Further, "perfluorinated" means substantially all of portions which may be fluorinated, in a group to be fluorinated, are fluorinated. For example, in a group obtained by perfluorinating a monovalent organic group having C—H portions, substantially all of the C—H portions will be C—F, and in a group obtained by perfluorinating a monovalent organic group having carbon-carbon unsaturated bonds, fluorine atoms are attached to substantially all of the unsaturated bonds.

The perfluorinated monovalent organic group may, for example, be a perfluoroalkyl group and may, specifically be —$CF_2CF_3$, —$CF_2CF_2CF_3$, —$CF_2CF_2CF_2CF_3$, —$CF(CF_3)_2$, —$CF_2CF(CF_3)_2$, —$CF(CF_3)CF_2CF_3$ or —$C(CF_3)_3$. Further, a group having a chlorine atom or a bromine atom bonded, such as —$CF_2CClF_2$, —$CF_2CBrF_2$ or —$CF_2CFClCF_2Cl$, may also be exemplified.

Further, the perfluorinated group containing an etheric oxygen atom may, for example, be a group having an etheric oxygen atom inserted between carbon-carbon atoms in the above exemplified group and may, for example, be —CF($CF_3$) [$OCF_2CF(CF_3)$]$_b OCF_2CF_2CF_3$ (wherein b is an integer of 0 or more, preferably an integer of 0 or from 1 to 5) or —($CF_2$)$_d OCF_3$ (wherein d is an integer of at least 1, preferably an integer of from 1 to 8).

In the present invention, a compound represented by the formula (3) will be referred to as a compound (3). Compounds represented by other formulae will be likewise referred to. Further, unless otherwise specified, the description of the compound (3) is applicable to the compound (3X) and the compound (3Y), and the description of the compound (4) is applicable to the compound (4X) and the compound (4Y).

The present invention provides the following novel compound (3):

$$A(\text{-G-Q-R})_n \quad (3)$$

The compound (3) is a compound wherein n groups represented by (-G-Q-R) are bonded to a group represented by A. A is a n-valent group wherein n hydrogen atoms of adamantane converted to connecting bonds, wherein hydrogen atoms not converted to connecting bonds, may be each substituted by an alkyl group.

Here, adamantane is a compound represented by the following formula:

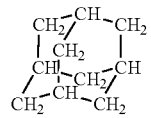

The carbon atoms constituting adamantane include secondary carbon atoms each having two hydrogen atoms bonded, and tertiary carbon atoms each having one hydrogen atom bonded thereto. And, a hydrogen atom which can be converted to a connecting bond may be a hydrogen atom bonded to a secondary carbon atom, or a hydrogen atom bonded to a tertiary carbon atom.

Further, the hydrogen atoms of adamantane not converted to connecting bonds may be each substituted by an alkyl group. The alkyl group is preferably a $C_{1-6}$ alkyl group, particularly preferably a methyl group. Further, the hydrogen atom substituted by such an alkyl group is preferably a hydrogen group bonded to a secondary carbon atom in a case where the carbon atom bonded to a (-G-Q-R) group is the secondary carbon atom.

The symbol n represents the number of bonds and the number of (-G-Q-R) groups and is an integer of from 1 to 4. From the availability of the compound, n is preferably 1 or 2. Further, the compound wherein n is 2 or more is a compound which can be advantageously produced in that the molecular weight increases, the vapor pressure decreases, control for the reaction of liquid phase fluorination tends to be easy, and the yield is high.

G is —$CH_2$— or a single bond, and G being a single bond means that A and Q are directly bonded to each other. Q is a —OCO— or —COO— group.

R is a fluorinated monovalent organic group, preferably a fluorinated monovalent saturated hydrocarbon group, or a fluorinated monovalent saturated hydrocarbon group containing an etheric oxygen atom, particularly preferably a fluorinated alkyl group, or a fluorinated alkyl group containing an etheric oxygen atom. Such a group having from 2 to 20 carbon atoms is preferred, and particularly preferred is a $C_{2-20}$ polyfluoroalkyl group or a $C_{2-20}$ polyfluoroalkyl group containing an etheric oxygen atom.

Further, R is preferably a perfluorinated group, and an example of such a perfluroinated group may be a perfluoroalkyl group, a perfluoro(partially chloroalkyl group), a perfluoro(partially bromoalkyl) group) or a perfluorinated alkyl group containing an etheric oxygen atom, preferably a perfluoroalkyl group or a perfluoroalkyl group containing an etheric oxygen atom, particularly preferably such a group having from 2 to 20 carbon atoms.

The carbon number of R is preferably a carbon number whereby the molecular weight of the compound (3) will be within the preferred molecular weight range which will be described hereinafter. In a usual case, the carbon number of R is preferably from 2 to 20, particularly preferably from 2 to 10.

Specific examples of R may be groups exemplified for the above perfluorinated monovalent organic group and exemplified for the above perfluorinated group containing an etheric oxygen atom.

The compound (3) is the following compound (3X) or the following compound (3Y).

A(-G-OCOR)$_n$          (3X)

A(-G-COOR)$_n$          (3Y)

In a case where n is 2 or more, (-G-Q-R) groups are preferably bonded to different carbon atoms, respectively, and they may be bonded only to secondary carbon atoms or only to tertiary carbon atoms, or may be bonded to both types of carbon atoms. However, (-G-Q-R) groups wherein G is a single bond, are preferably present as bonded only to tertiary carbon atoms.

The compound (3X) is the following compound (3X-A) or the following compound (3X-B):

A(—CH$_2$OCOR)$_n$          (3X-A)

A(—OCOR)$_n$          (3X-B)

The compound (3Y) is the following compound (3Y-A) or the following compound (3Y-B):

A(—CH$_2$COOR)$_n$          (3Y-A)

A(—COOR)$_n$          (3Y-B)

In the compound (3X) and the compound (3Y), n is preferably 1 or 2. When n is 1, the position of the carbon atom to which the (-G-Q-R) group is bonded, is not limited. When n is 2, the (-G-Q-R) groups are preferably bonded to different carbon atoms.

The following compounds may be mentioned as examples of the compound (3):

Examples of the Compound (3) wherein n=1

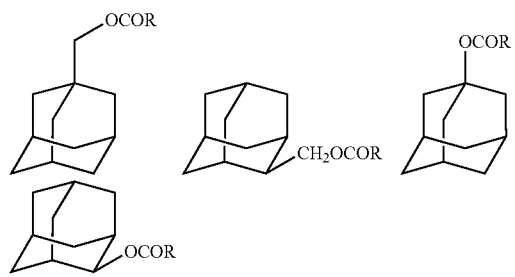

Examples of the Compound (3) wherein n=2

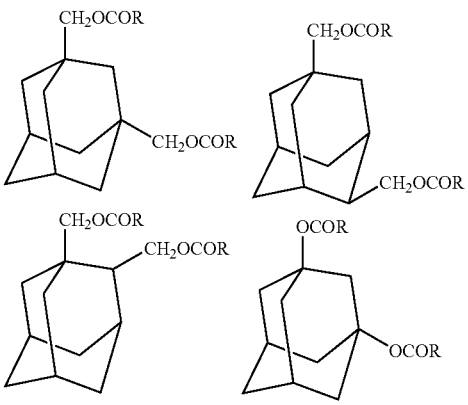

The compound (3) is useful as an intermediate for the production of the compound (4). The compound (4) can be produced by a liquid phase fluorination reaction of the compound (3). In order to let the liquid phase fluorination reaction proceed smoothly, the fluorine content of the compound (3) is adjusted to be preferably from 20 to 60 mass %, particularly preferably from 25 to 55 mass %. Further, the molecular weight of the compound (3) is preferably within a range of from 200 to 1,100, particularly preferably within a range of from 300 to 800.

With the compound (3) having the fluorine content within the above specified range, the solubility in the liquid phase at the time of the fluorination reaction will be remarkably improved, whereby there will be a merit such that the operation efficiency of the liquid phase fluorination reaction and the reaction yield will be improved, and the economical efficiency will be excellent. Further, when the molecular weight of the compound (3) is at least 200 (more preferably at least 300), there will be a merit such that a risk of a decomposition reaction taking place by the gas phase fluorination reaction can be avoided, and when the molecular weight is at most 1,100 (more preferably at most 800), there will be a merit such that the handling of the compound and the purification of the product will be easy.

The present invention provides the following novel compound (4).

A$^f$(-G$^f$-Q-R$^f$)$_n$          (4)

R$^f$ is a fluorinated monovalent organic group. A$^f$ is the above group (A) wherein at least one of hydrogen atoms is substituted by a fluorine atom. A$^f$ is preferably the group (A) wherein at least 50% of hydrogen atoms are substituted by fluorine atoms, particularly preferably the group wherein at least 90% of hydrogen atoms are substituted by fluorine atoms, most preferably a perfluoro group wherein 100% is substituted (A$^f$ in such a case will be represented by A$^F$). G$^f$ is a single bond or —CF$_2$—. Q is as defined above.

The compound (4) is the following compound (4X) or the following compound (4Y). Further, the compound (4X) is the following compound (4X-A) or the following compound (4X-B). The compound (4Y) is the following compound (4Y-A) or the following compound (4Y-B).

A$^f$(-G$^f$-OCO—R$^f$)$_n$          (4X)

A$^f$(-G$^f$-OCO—R$^f$)$_n$          (4Y)

A$^f$(—CF$_2$OCOR$^f$)$_n$          (4X-A)

$$A^f(\text{—OCOR}^f)_n \quad (4\text{X-B})$$

$$A^f(\text{—CF}_2\text{COOR}^f)_n \quad (4\text{Y-A})$$

$$A^f(\text{—COOR}^f)_n \quad (4\text{Y-B})$$

Here, $A^f$ is preferably $A^F$. $R^f$ is a fluorinated monovalent organic group, and the preferred embodiment of such a group is the same as that of R. Namely, a perfluoroalkyl group or a perfluoroalkyl group containing an etheric oxygen atom is preferred, and a $C_{2-20}$ perfluoroalkyl group or a $C_{2-20}$ perfluoroalkyl group containing an etheric oxygen atom, is particularly preferred. Symbol n has the same meaning as in the compound (3), and the preferred embodiment is also the same.

In the compound (4X) and the compound (4Y), n is preferably 1 or 2, and in a case where n is 1, the position of the carbon atom to which the ($-G^f$-Q-$R^f$) group is bonded, is not limited. In a case where n is 2, the ($-G^f$-Q-$R^f$) groups are preferably bonded to different carbon atoms. Further, in the formula (4X-B), (—OCOR$^f$) groups are preferably bonded to tertiary carbon atoms, or to secondary carbon atoms, wherein the hydrogen atoms bonded to such carbon atoms are substituted by fluoroalkyl groups (preferably by perfluoroalkyl groups, particularly preferably by trifluoromethyl groups).

A specific example of the compound (4) may be the above-mentioned compound (3) wherein at least one of hydrogen atoms is substituted by a fluorine atom, preferably the compound wherein all hydrogen atoms are substituted by fluorine atoms.

The following compounds may be mentioned as examples of the compound (4). Here, $R^F$ is a perfluoroalkyl group or a perfluoroalkyl group containing an etheric oxygen atom.

Examples of the Compound (4) wherein n is 1

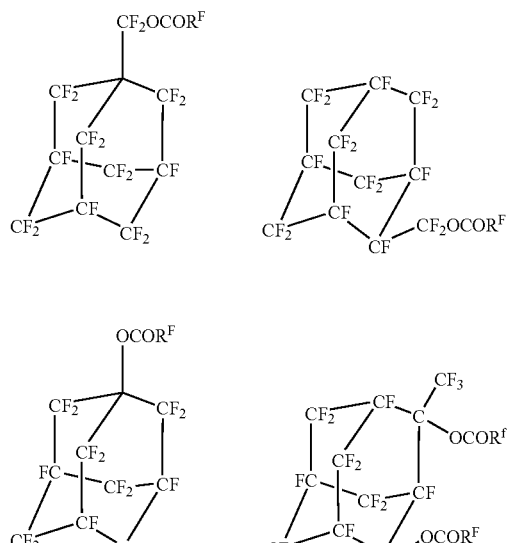

Examples of the Compound (4) wherein n is 2

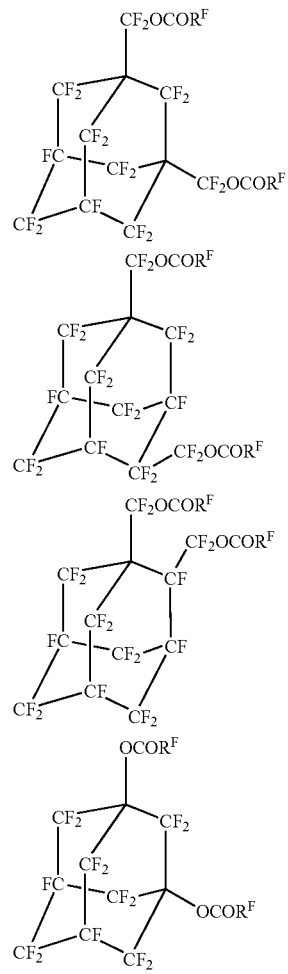

The compound (3) and the compound (4) of the present invention are preferably produced by the following method (X) or method (Y).

Method (X): A method wherein a compound (3X) is obtained by an esterification reaction of the following compound (1X) with the following compound (2X), and then, the compound (3X) is fluorinated by liquid phase fluorination to obtain the compound (4X).

Method (Y): A method wherein a compound (3Y) is obtained by an esterification reaction of the following compound (1Y) with the following compound (2Y), and then, the compound (3Y) is fluorinated by liquid phase fluorination to obtain the compound (4Y).

Here, the symbols in the following formulae have the same meanings as defined above, and Z is a halogen atom, preferably a fluorine atom or a chlorine atom.

$$A(\text{-G-OH})_n \quad (1\text{X})$$

$$R\text{-COZ} \quad (2\text{X})$$

$$A(\text{-G-OCOR})_n \quad (3\text{X})$$

$$A^f(\text{-}G^f\text{-OCO—}R^f) \quad (4\text{X})$$

$$A(\text{-G-COZ})_n \quad (1Y)$$

$$R\text{—OH} \quad (2Y)$$

$$A(\text{-G-COOR})_n \quad (3Y)$$

$$A^f(\text{-}G^f\text{-COO—}R^f)_n \quad (4Y)$$

The compound (1X), the compound (2X), the compound (1Y) and the compound (2Y) can be produced by known methods or are available as commercial products. For example, the compound (2X) wherein Z is a fluorine atom, can be produced, for example, by an oligomerization reaction of hexafluoropropylene or by a method disclosed in WO00/56694 by the present applicant.

The esterification reaction of the compound (1X) with the compound (2X), and the esterification reaction of the compound (1Y) with the compound (2Y) can be carried out under the conditions of known esterification reactions. The lower limit of the reaction temperatures is usually preferably −50° C., and the upper limit is preferably +100° C. The reaction time may optionally be changed depending upon the supply rates of the materials and the amount of the compound. The reaction pressure is preferably from atmospheric pressure to 2 MPa (gauge pressure, hereinafter, the pressure is represented by a gauge pressure).

In the esterification reaction, the amount of the compound (2X) to the compound (1X) is preferably at least n mols. The amount of the compound (2Y) to the compound (1Y) is preferably at most n mols. Specifically, the amount of the compound (2X) is particularly preferably from 1 to 2 times by mol, especially preferably from 1 to 1.1 times by mol, relative to the compound (1X). The amount of the compound (1Y) is particularly preferably from 0.5 to 1 time by mol, especially preferably from 0.9 to 1.0 time by mol, relative to the compound (2Y). When the reaction is carried out in such an amount, a non-reacted hydroxyl group-containing compound will remain in the reaction product of the esterification reaction, and a side reaction in the fluorination in the subsequent step can be avoided, and the purification process of the compound (3) can be simplified.

The product of the esterification reaction is preferably purified from such a viewpoint that the fluorination reaction is smoothly carried out. Especially when the product of the esterification reaction contains a hydroxyl group-containing compound, it is preferred that such a compound is preliminarily removed by purification. The purification method may, for example, be a distillation method, a method wherein the product is treated with e.g. water, followed by liquid separation, a method wherein extraction is carried out with a suitable organic solvent, followed by distillation, or silica gel column chromatography.

In the esterification reaction, hydrofluoric acid (HF) will be formed, and an alkali metal fluoride (NaF or KF is, for example, preferred) or a trialkylamine, may be present as a HF capturing agent in the reaction system. The amount of the HF capturing agent is preferably from 0.1 to 10 times by mol relative to the theoretical amount of generated HF. In a case where no HF capturing agent is used, it is preferred that the reaction is carried out at a reaction temperature where HF can be evaporated, so that HF is discharged out of the reaction system as accompanied with a nitrogen stream.

Further, a method may be employed wherein without using a HF scavenger, HF is discharged out of the reaction system as accompanied with a nitrogen stream, and it is preferred to employ such a method in that the crude liquid may thereby be employed as it is in the next fluorination step.

The compound (3) can then be converted to the compound (4) by a liquid phase fluorination reaction. In a case where R in the compound (3) is a group which can not be fluorinated (i.e. R is a perfluoro monovalent organic group), $R^f$ in the compound (4) is the same group as R (i.e. $R^F$ group). The fluorination can be carried out by a fluorination method employing cobalt fluoride or by an electrochemical fluorination method. However, it is preferred to carry out the fluorination by a liquid phase fluorination method wherein the compound is reacted with fluorine ($F_2$) in a liquid phase, since the yield in the fluorination reaction is remarkably high.

The liquid phase in the liquid phase fluorination method may be the compound (3), but it is preferred to employ a solvent which is not concerned with the product or the reaction.

As such a solvent, a solvent inert to the fluorination reaction is preferred, and it is particularly preferred to employ a solvent in which the solubility of the compound (3) is high, and it is especially preferred to employ a solvent which is capable of dissolving at least 1 mass %, particularly preferably at least 5 mass %, of the compound (3).

The solvent to be used for the fluorination reaction may, for example, be a known solvent to be used as a solvent for liquid phase fluorination, the compound (2F) which will be described hereinafter, the compound (4X-A) wherein $R^f$ is $R^F$, the compound (4X-B) wherein $R^f$ is $R^F$, the compound (5X-A) as described hereinafter (wherein $R^f$ is $R^F$) and the compound (5X-B) as described hereinafter (wherein $R^f$ is $R^F$). The known solvent may, for example, be a chlorofluorocarbon such as $CF_2ClCFCl_2$, perfluorotributylamine, or a fluorocarbon such as perfluoro(2-butyltetrahydrofuran). Among them, the solvent is preferably the compound (2F), the compound (4X-A) or the compound (4X-B), since there is a merit such that the post treatment will be easy. The amount of the solvent is preferably at least 5 times by mass, particularly preferably from $1 \times 10^1$ to $1 \times 10^5$ times by mass, relative to the total mass of the compound (3).

The reaction system for the fluorination reaction may be a batch system or a continuous system. For example, a method may be mentioned wherein a solvent for a fluorination reaction is charged and stirred in a reactor, and then, fluorine gas and the compound (3) are continuously supplied into the solvent for the fluorination reaction in a prescribed molar ratio.

As fluorine, it is preferred to employ fluorine gas itself or fluorine gas diluted with an inert gas. The inert gas is preferably nitrogen gas or helium gas, and nitrogen gas is particularly preferred from the economical reason. The amount of fluorine gas in the nitrogen gas is not particularly limited, but from the viewpoint of the efficiency, it is preferably at least 10 vol %, particularly preferably at least 20 vol %.

Fluorine to be used for the fluorination reaction is preferably maintained so that the amount of fluorine ($F_2$) to the amount of hydrogen atoms contained in the compound (3) will be always in excess by equivalent from the beginning to the end of the reaction. Particularly, it is preferred from the viewpoint of the selectivity to maintain the amount of fluorine to hydrogen atoms to be at least 1.05 times by equivalent (i.e. at least 1.05 times by mol), and it is further preferred from the viewpoint of the selectivity to maintain it to be at least twice by equivalent (i.e. at least twice by mol). Further, in order to let the amount of fluorine be in excess by equivalent also at the initiation of the reaction, it is preferred to let fluorine preliminarily be dissolved in a sufficient amount in the solvent for the fluorination reaction to be used at the beginning of the reaction.

Further, it is necessary to carry out the liquid phase fluorination reaction without breaking the ester bond in the compound (3), and it is preferred to set the lower limit of the reaction temperature at whichever is lower between −60° C. and the boiling point of the compound (3). In a usual case, the reaction temperature is particularly preferably from −50° C. to +100° C., especially preferably from −20° C. to +50° C., in view of the reaction yield, the selectivity and the industrial operation efficiency. The reaction pressure for the fluorination reaction is not particularly limited, and it is usually preferred to adjust the pressure to be from atmospheric pressure to 2 MPa from the viewpoint of the reaction yield, the selectivity and the industrial operation efficiency.

Further, in order to let the fluorination reaction proceed efficiently, it is preferred to add a C—H bond-containing compound such as benzene or toluene to the reaction system, to let the compound (3) stay for a long time in a reaction system or to carry out ultraviolet irradiation. Such an operation is preferably carried out at a later stage of the fluorination reaction.

The fluorination reaction of the present invention is a reaction wherein at least one of hydrogen atoms bonded to carbon atoms in the compound represented by the formula (3) is substituted by a fluorine atom, and preferably, at least 50%, particularly preferably at least 90%, especially preferably at least 95%, of the number of hydrogen atoms, is substituted. However, in a case where G is —CH$_2$—, it is preferred to continue the fluorination until it is converted to —CF$_2$—. Such —CH$_2$— is susceptible to fluorination and will be fluorinated more preferentially than hydrogen atoms in A. Further, the objective compound of the present invention is preferably perfluorinated, but a compound wherein some hydrogen atoms still remain, may also be useful depending upon the particular purpose.

In the liquid phase fluorination, a hydrogen atom will be substituted by a fluorine atom to form HF as a by-product. For the purpose of removing such HF, it is preferred to let a HF-scavenger (preferably NaF) be present in the reaction system and to let the HF-scavenger contact with the outlet gas at the gas outlet of the reactor, or to cool the outlet gas thereby to condense and recover HF. Otherwise, HF may be discharged out of the reaction system as accompanied with an inert gas such as nitrogen gas and then subjected to alkali treatment. In a case where a HF-scavenger is to be used, its amount is preferably from 1 to 20 times by mol, more preferably from 1 to 5 times by mol, relative to the total amount of hydrogen atoms present in the compound (3).

The reaction product of the fluorination reaction may be used as it is in the subsequent step or may be purified to a high purity product. As a purification method, a method of distilling a crude product under atmospheric pressure or under reduced pressure may, for example, be mentioned.

In the fluorination reaction of the compound (3), the compound (4) will be formed. The compound (4) is a useful novel compound by itself, but may be led to the following various useful compounds (5X) or (5Y).

  (5X)

  (5Y)

Here, $A^f$ and n are as defined above, and $G^p$ is —COF, —OH, or a keto group formed together with the carbon atom in $A^f$ to which $G^p$ is bonded. Further, in a case where n is 2 or more, the structures of -$G^p$ in the formula (5) may be the same or different.

Methods for producing compounds (5) are classified by the structures of -$G^f$ in the compounds (4X) and (4Y), and it is preferred to adopt the following method 1 or 2.

Method 1: A method for obtaining the following compound (5X-A), which comprises carrying out a decomposition reaction of an ester bond in the compound (4X-A) which is the compound (4X) wherein -$G^f$- is —CF$_2$—:

  (4X-A)

  (5X-A)

Method 2: A method for obtaining the following compound (5X-B1) or the following compound (5X-B2), which comprises carrying out hydrolysis or alcoholysis of the compound (4X-B) which is the compound (4X) wherein -$G^f$- is a single bond:

  (4X-B)

  (5X-B1)

  (5X-B2)

Method 3: A method for obtaining the following compound (5Y-A), which comprises carrying out a decomposition reaction of an ester bond in the compound (4Y-A) which is the compound (4Y) wherein -$G^f$- is —CF$_2$—:

  (4Y-A)

  (5Y-A)

The decomposition reaction of an ester bond in method 1 and method 3 is a known reaction. The decomposition reaction of an ester bond is preferably carried out by a thermal decomposition reaction or by a decomposition reaction carried out in the presence a nucleophilic agent or an electrophilic agent. The thermal decomposition reaction is preferably carried out by a liquid phase reaction.

The decomposition reaction of an ester bond will be described with reference to the case of the compound (4X-A) as an example. The liquid phase decomposition method is preferably carried out by a method wherein a liquefied compound (4X-A) is heated. The product of the decomposition reaction may be withdrawn from the reactor all at once. Otherwise, utilizing such a nature that the formed compound (5X-A) usually has a lower boiling point than that of the compound (4X-A), the reaction may be carried out by using a reactor equipped with a distillation column, while withdrawing the product by distillation. The reaction temperature for the liquid phase thermal decomposition method is preferably from 50 to 300° C., particularly preferably from 100 to 250° C. The reaction pressure in the liquid phase thermal decomposition method is not particularly limited.

The liquid phase thermal decomposition method may be carried out in the absence of any solvent or in the presence of a solvent for the decomposition reaction, and it is preferably carried out in the absence of any solvent. In a case where a solvent for the decomposition reaction is to be used, it is preferred to use such a solvent in an amount of from 0.1 to 10 times by mass relative to the compound (4X-A).

In a case where the decomposition reaction of an ester bond is to be carried out by a method of reacting it with a nucleophilic agent or an electrophilic agent in the liquid phase, the reaction may be carried out in the absence of any solvent or in the presence of a solvent for the decomposition reaction, and it is preferably carried out in the absence of any solvent. If the reaction is carried out in the absence of any solvent, the fluorination reaction product itself will serve as a solvent, whereby it is possible to save the trouble of separating a solvent from the reaction product. The method of employing a nucleophilic agent or an electrophilic agent is also preferably carried out while carrying out distillation by a reactor equipped with a distillation column.

As the nucleophilic agent, F⁻ is preferred, and particularly preferred is F⁻ derived from an alkali metal fluoride. The alkali metal fluoride is preferably NaF, NaHF$_2$, KF or CsF. From the viewpoint of the economical efficiency, NaF is particularly preferred, and from the viewpoint of the reactivity, KF is particularly preferred. Further, the initial amount of the nucleophilic agent in the reaction may be a catalytic amount or an amount in excess. The amount of a nucleophilic agent such as F⁻ is preferably from 1 to 500 mol %, particularly preferably from 1 to 100 mol %, especially preferably from 5 to 50 mol %, based on the fluorination reaction product. The lower limit of the reaction temperature is preferably −30° C., and the upper limit is preferably from −20° C. to 250° C. In the decomposition reaction of an ester bond of the compound (4X-A), the following compound (2f) (preferably the following compound (2F)) will be formed together with the compound (5X-A). Here, $R^f$ and $R^F$ are as defined above.

R$^f$COF (2f)

R$^F$COF (2F)

The compound (2f) is preferably separated from the compound (5X-A) in the reaction product of the ester bond by a distillation method. A part or all of the separated compound (2f) may preferably be used as the compound (2X) to be used for the preparation of the above-mentioned compound (3).

The following compounds may be mentioned as specific examples of the compound (5X-A):

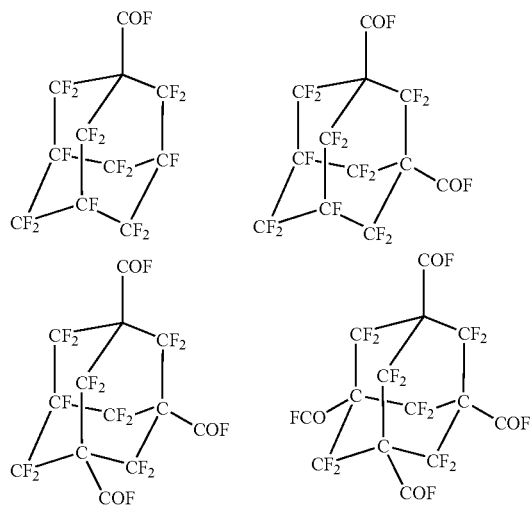

Method 2 is preferably a decomposition reaction which is carried out in the presence of a compound represented by the formula $R^H$—OH (wherein $R^H$ is a hydrogen atom or a monovalent hydrocarbon group.). In a case where $R^H$ is a hydrogen atom, the reaction will be hydrolysis, and in a case where $R^H$ is a monovalent hydrocarbon group, the reaction will be alcoholysis. In a case where $R^H$ is a monovalent hydrocarbon group, it may, for example, be an alkyl group, a cycloalkyl group, or a group wherein one of hydrogen atoms of adamantane is converted to a connecting bond. The carbon number of such a group is preferably from 1 to 10. In a case where the compound represented by $R^H$—OH is an alcohol, it is preferably a primary or secondary alcohol, particularly preferably a cycloalkanol. As a specific example of the primary alcohol, methanol, ethanol, 2-ethylhexyl alcohol or octanol may be mentioned, and as a specific example of the secondary alcohol, 2-propanol, 2-butanol or cyclohexanol may, for example, be mentioned. A C$_{6-10}$ alcohol is preferred, and it is particularly preferred to select it from alcohols having boiling points higher than the compound (5X-B) and the after-mentioned compound (3X-C).

The decomposition reaction in method 2, is preferably carried out under an acidic or basic condition. As the acid to be used for the decomposition reaction under an acidic condition, hydrochloric acid or sulfuric acid may, for example, be preferred. As the base to be used for the decomposition reaction under a basic condition, a hydroxide of an alkali metal or a hydroxide of an alkaline earth metal is preferred. As the alkali metal hydroxide, NaOH, KOH or CsOH is preferred, and from the viewpoint of the economical efficiency, NaOH is particularly preferred. The temperature for the decomposition reaction is preferably from 50 to 300° C., particularly preferably from 100 to 250° C. The reaction pressure is not particularly limited.

The decomposition reaction of the compound (4X-B) may be carried out in the presence of a solvent for the reaction. When a solvent for the decomposition reaction is to be used, it is preferred to use such a solvent in an amount of from 0.1 to 10 times by mass relative to the compound (4X-B). Further, in a case where the compound represented by $R^H$—OH is used in an excess amount, such a compound may serve also as a solvent.

In a case where in the compound (4X-B) in method 2, the carbon atoms to which (—OCOR$^f$) groups are bonded, are tertiary carbon atoms of adamantane, the compound (5X-B1) will be formed. On the other hand, in a case where fluorine atoms are bonded to the carbon atoms in A$^f$ to which (—OCOR$^f$) groups are bonded, the compound (5X-B2) will be formed. The (═O) portion in the formula (5X-B2) means that an oxygen atom forms a keto group together with the carbon atom to which (—OCOR$^f$)$^p$ is bonded.

In a case where water remains in such a hydrolyzate, the water may be added to the compound (5X-B2) to form the following compound (5X-B2-OH). In a case where a compound represented by RH$^H$—OH remains in the alcoholysis product, $R^H$—OH may be added to the compound (5X-B2) to form the following compound (5X-B2-OR). Here, the symbols in the following formulae have the same meanings as defined above, and k is an integer of from 1 to 4, and n≧k.

A$^f$[(OH)$_2$]$_k$(═O)$_{n-k}$ (5X-B2-OH)

A$^f$[(OR$^H$)$_2$]$_k$(═O)$_{n-k}$ (5X-B2-OR)

Further, in the decomposition reaction of the compound (4X-B) in method 2, the following compound (3X-C) will also be formed. Here, $R^F$ and $R^H$ have the same meanings as defined above.

R$^F$COOR$^H$ (3X-C)

In a case where the compound (3X-C) is formed, it is preferred to separate the compound (3X-C) and the compound (5X-B). As the separation method, distillation may, for example, be preferred. Further, decomposition reaction of the compound (4X-B) may be carried out in the reactive distillation system to carry out the reaction while withdrawing the compound (5X-B), thereby to separate the compound (5X-B).

The following compounds may be mentioned as specific examples of the compound (5X-B1):

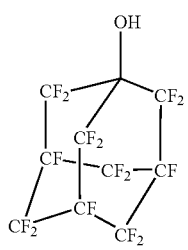 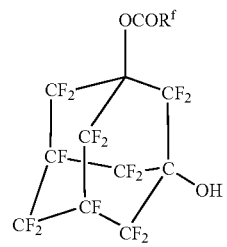

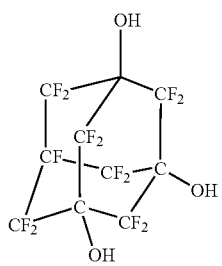 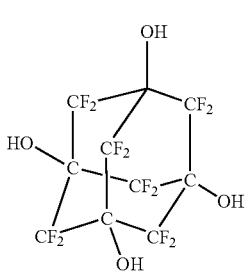

The following compounds may be mentioned as specific examples of the compound (5X-B2):

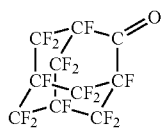 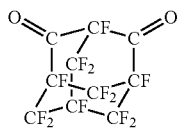

The compound (5X) obtained by the method of the present invention is useful as an intermediate for various functional materials. For example, a compound obtained by an esterification reaction of the hydroxyl group of the compound (5X-B1) with acrylic acid or methacrylic acid, is an acrylate useful as a comonomer for an etching resistant polymer, and the following compound may be mentioned as a specific example of such a compound:

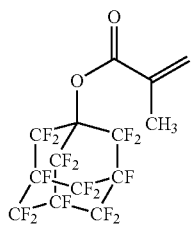

Further, a compound obtained by an esterification reaction of a —COF group of the compound (5X-A) with propen-2-ol, is an acrylate useful as a comonomer for an etching resistant polymer, and the following compound may be mentioned as a specific example of such a compound.

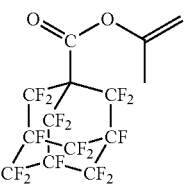

The following compounds may be mentioned as preferred embodiments in the present invention.

Examples of Compound (3):

(3a)

$CH_2OCOCF(CF_3)OCF_2CF_2CF_3$

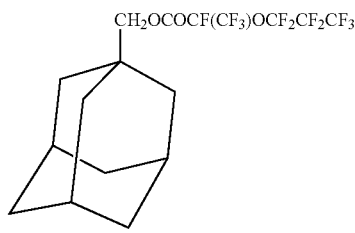

(3b)

$OCOCF(CF_3)OCF_2CF_2CF_3$

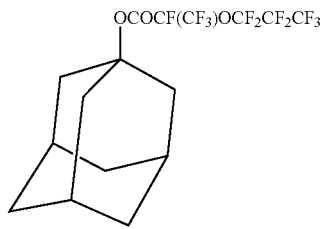

(3c)

$CH_3$
$OCOCF(CF_3)OCF_2CF_2CF_3$

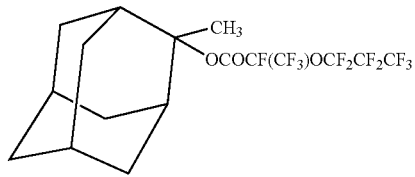

(3d)

$COOCH_2CF(CF_3)OCF_2CF(CF_3)OCF_2CF_2CF_3$

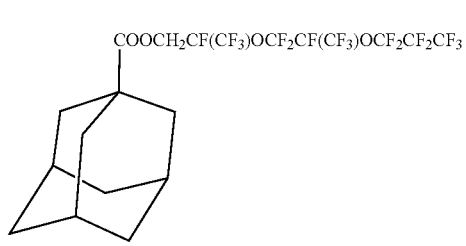

Examples of Compound (4):

(4a)

$CF_2OCOCF(CF_3)OCF_2CF_2CF_3$

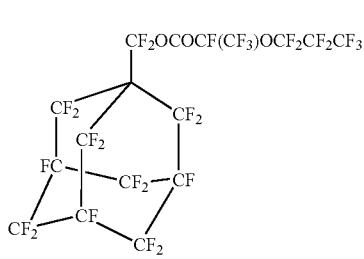

-continued

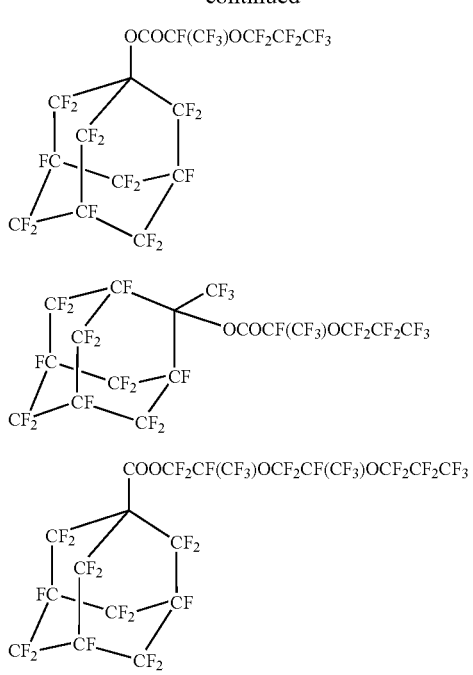

Examples of Compound (5):

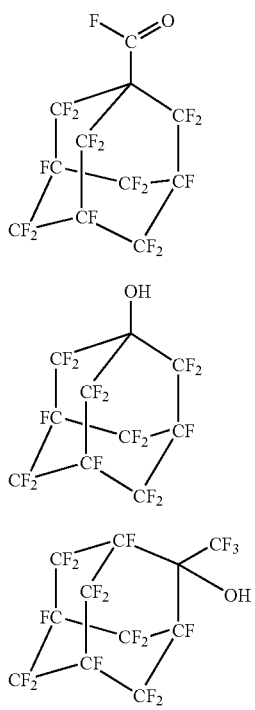

When the adamantane derivatives of the present invention are used as photolithographic material, they provide a high level of etching resistance. The reason is considered to be such that in an adamantane skeleton having a structure wherein cyclic compounds are bonded to each other, even if part of bonds is broken by a laser beam, the compound hardly undergoes decomposition and remains to be stable.

Further, the adamantane derivatives of the present invention essentially have C—F structures, and such structures are superior to C—H structures in light transmittance, and thus they can be material having both high levels of etching resistance and light transmittance.

EXAMPLES

Now, the present invention will be described in further detail with reference to Examples. However, it should be understood that the present invention is by no means restricted to such specific Examples.

In Examples, 1,1,2-trichloro-1,2,2-trifluoroethane will be referred to as R-113, and dichloropentafluoropropane as R-225. As R-225, a mixed product of $CF_3CF_2CHCl_2$ and $CF_2ClCF_2CHFCl$ was used. Gas chromatography will be referred to as GC, and the results in the GC analyses are shown by the peak area ratios. Gas chromatography mass spectrometry will be referred to as GC-MS. The pressure is shown by a gauge pressure.

Example 1

Production of Compound (5a)

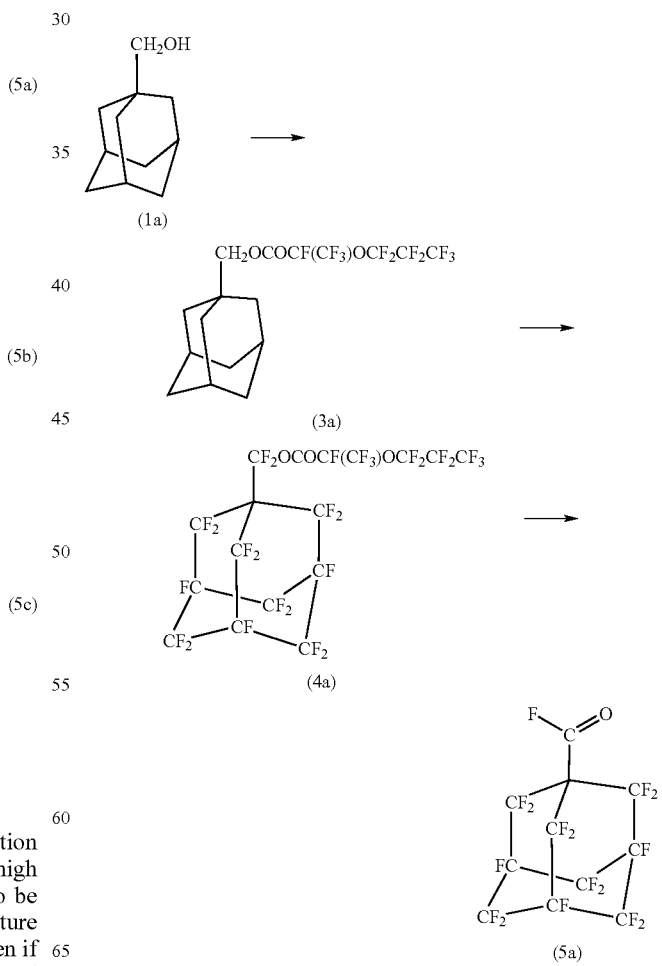

Example 1-1

Preparation of Compound (3a)

Compound (1a) (8 g) and chloroform (40 mL) were put into a flask and stirred while bubbling nitrogen gas. FCOCF(CF$_3$)OCF$_2$CF$_2$CF$_3$ (25.5 g) was dropwise added over a period of one hour while maintaining the internal temperature at 30° C. After completion of the dropwise addition, the mixture was stirred at 30° C. for 3 hours, and a saturated sodium hydrogen carbonate aqueous solution (50 ml) was added at an internal temperature of at most 15° C.

The obtained crude liquid was subjected to liquid separation, and an organic layer was obtained. Further, the organic layer was washed twice with water (50 ml) and dried over magnesium sulfate, followed by filtration to obtain a crude liquid. The crude liquid was purified by silica gel column chromatography (developing solvent: R-225) to obtain the following compound (3a) (20.4 g). The NMR spectrum data were as follows.

$^1$H-NMR (300.4 MHz, solvent: CDCl$_3$, standard: TMS) δ (ppm): 1.50 to 1.80 (m, 12H), 2.01 (bs, 3H), 3.87 (d, J=10.7 Hz, 1H), 4.04 (d, J=10.7 Hz, 1H). $^{19}$F-NMR (282.7 MHz, solvent: CDCl$_3$, standard: CFCl$_3$) δ (ppm): −80.2 (1F), −81.3 (3F), −82.0 (3F), −86.4 (m, 1F), −129.5 (2F), −131.3 (1F).

Example 1-2

Fluorination Reaction (Case 1) of Compound (3a)

Into a 500 mL autoclave made of nickel, R-113 (312 g) was introduced, stirred and maintained at 25° C. At a gas outlet of the autoclave, a condenser maintained at 25° C., a NaF pellet packed layer and a condenser maintained at 10° C. were installed in series. Further, from the condenser maintained at −10° C., a liquid-returning line was installed to return the condensed liquid to the autoclave. After blowing nitrogen gas for 1.0 hour, fluorine gas diluted to 20% with nitrogen gas (hereinafter referred to as 20% fluorine gas) was blown at a flow rate of 9.97 L/hr for one hour. Then, while blowing 20% fluorine gas at the same flow rate, a solution having the compound (3a) (5.0 g) obtained in Example 1-1 dissolved in R-113 (102 g), was injected over a period of 4.7 hours.

Then, while blowing 20% fluorine gas at the same flow rate and maintaining the pressure of the autoclave at 0.15 MPa, a R-113 solution having a benzene concentration of 0.01 g/ml (hereinafter referred to as the benzene solution) was injected in an amount of 9 ml while raising the internal temperature of the autoclave from 25° C. to 40° C., whereupon the benzene inlet of the autoclave was closed, and stirring was continued for 0.3 hour. Then, while maintaining the autoclave pressure at 0.15 MPa and the autoclave internal temperature at 40° C., the benzene solution (6 ml) was injected, and stirring was continued for 0.3 hour. Then, while maintaining the autoclave pressure at 0.15 MPa and the autoclave internal temperature at 40° C., the benzene solution (8.5 ml) was injected, and stirring was further continued for 1.0 hour. The total amount of benzene injected was 0.24 g, and the total amount of R-113 injected was 23.5 ml. Further, nitrogen gas was blown for 1.0 hour. The desired product was quantified by $^{19}$F-NMR (internal standard: C$_6$F$_6$), whereby the yield of the compound (4a) as a completely fluorinated product was 29%. Further, a partially fluorinated product of the compound (3a) was formed in a yield of 71%.

$^{19}$F-NMR (376.0 MHz, solvent: CDCl$_3$, standard: CFCl$_3$) δ (ppm): −61.9 (2F), −79.0 to −81.0 (1F), −82.0 (3F), −82.1 (3F), −85.5 to −88.0 (1F), −109.0 to −116.0 (6F), −117.0 to −125.0 (6F), −130.1 (2F), −131.6 to −133.5 (1F), −217.0 to −222.0 (3F).

$^1$H-NMR (399.8 MHz, solvent: CDCl$_3$, standard: TMS) δ (ppm): 3.79 (m, 1H), 5.30 to 5.70 (m, 1H), 7.00 to 7.40 (m, 1H).

Example 1-3

Preparation (Case 2) of Compound (4) by Liquid Phase Fluorination

The same autoclave as in Example 1-2 was prepared, and 20% fluorine gas was blown at a flow rate of 10.60 L/hr for one hour. While blowing 20% fluorine gas at the same flow rate, a solution having the compound (3a) (5.0 g) obtained in Example 1-1 dissolved in R-113 (200 g), was injected over a period of 6.5 hours.

Then, while blowing 20% fluorine gas at the same flow rate and maintaining the autoclave pressure at 0.15 MPa, a R-113 solution of compound (3a) (0.01 g/ml) was injected in an amount of 9 ml while raising the temperature from 25° C. to 40° C., whereupon the benzene inlet of the autoclave was closed, and stirring was continued for 0.23 hour. Then, while maintaining the autoclave pressure at 0.15 MPa and the autoclave internal temperature at 40° C., the benzene solution (6 ml) was injected, and stirring was continued for 0.3 hour. Then, the same operation was carried out three times. Further, stirring was continued for 0.7 hour. The total amount of benzene injected was 0.35 g, and the total amount of R-113 injected was 33.0 ml. Further; nitrogen gas was blown for 1.0 hour. The desired product was quantified by $^{19}$F-NMR (internal standard: C$_6$F$_6$), whereby the yield of the compound (4a) was 61%.

$^{19}$F-NMR (376.0 MHz, solvent: CDCl$_3$, standard: CFCl$_3$) δ (ppm): −61.9 (2F), −80.4 (1F), −82.0 (3F), −82.1 (3F), −86.1 (1F), −110.7 (6F), −121.1 (6F), −130.1 (2F), −131.8 (1F), −219.5 (3F).

Example 1-4

Preparation of Compound (5a) by Liquid Phase Thermal Decomposition

Compound (4a) (5.3 g) obtained in Example 1-3 was charged together with KF powder (0.3 g) into a flask and heated in an oil bath at from 80 to 90° C. for 4 hours with vigorous stirring. At the top of the flask, a reflux condenser adjusted at the temperature of 20° C. and a pack made of a fluorine resin film (Tedler Pack, tradename, manufactured by Du Pont) were installed in series. After cooling, a liquid sample (3.4 g) was recovered. As a result of the analyses by GC-MS and $^{19}$F-NMR, the liquid sample was confirmed to contain compound (5a) and CF$_3$CF(OCF$_2$CF$_2$CF$_3$)COF as the main products.

$^{19}$F-NMR (376.0 MHz, solvent: CDCl$_3$, standard: CFCl$_3$) δ (ppm): 55.9 (1 F), −110.0 (6 F), −120.5 (6 F), −218.9 (3 F).

Example 2

Production of Compound (5b)

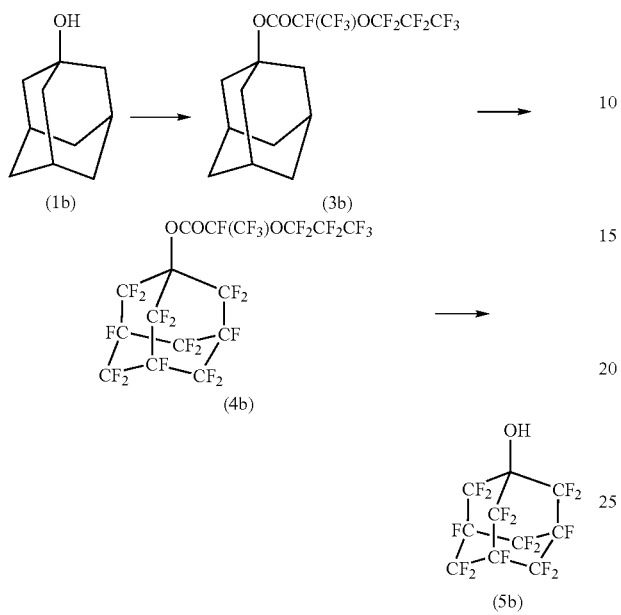

Example 2-1

Production of Compound (3b) by Esterification Reaction 1-adamantanol (3.09 g, 20.3 mmol) and sodium fluoride (0.95 g, 22.6 mmol) were put into a 50 mL round-bottomed flask, and $CF_3(CF_2)_2OCF(CF_3)COF$ (9.94 g, 29.9 mmol) was dropwise added at room temperature with stirring. After completion of the dropwise addition, stirring was carried out while raising the temperature to 50° C., and stirring was continued for 9 hours while maintaining the internal temperature at from 45 to 50° C. R-225 was added for dilution, then sodium fluoride was removed by filter paper, followed by washing with water, whereupon magnesium sulfate was added, and the mixture was left to stand overnight. Magnesium sulfate was removed by filtration, and the filtrate was condensed by an evaporator to obtain 8.80 g of a crude liquid. As a result of analyses by GC and NMR, it was confirmed that compound (3b) was formed at a selectivity of 99.8% and in a yield of 93.2%.

$^1$H-NMR (300.4 MHz, solvent: $CDCl_3$, standard: TMS) δ (ppm): 1.69 (s, 6 H), 2.15 (s, 6 H), 2.24 (s, 3 H).

$^{19}$F-NMR(282.7 MHz, solvent: $CDCl_3$, standard: $CFCl_3$) δ (ppm): −79.8 to −80.4 (1F), −81.7 (3F), −82.4 (3F), −86.4 to −87.0 (1F), −130.2 (2F), −131.7 (1F).

Example 2-2

Production of Compound (4b) by Fluorination Reaction

The same autoclave as in Example 1-2 was prepared, and after blowing 20% diluted fluorine gas at room temperature at a flow rate of 13.22 L/hr for 30 minutes, the internal pressure of the autoclave was raised to 0.15 MPa, whereupon the same gas was blown for further 30 minutes. Then, while blowing the 20% diluted fluorine gas at the same flow rate, a solution having compound (3b) (5 g) obtained in Example 2-1 dissolved in R-113 (100 g), was injected over a period of 4.2 hours.

A reaction was carried out under the same conditions as in Example 1-2 (provided that the benzene injection was carried out three times, and the total amount of benzene injected was 0.33 g, and the total amount of R-113 injected was 33 mL). After the reaction, the internal pressure of the reactor was adjusted to atmospheric pressure, and nitrogen gas was blown for one hour. The product was analyzed by $^{19}$F-NMR, whereby it was confirmed that compound (4b) was contained in a yield of 83%.

$^{19}$F-NMR (282.7 MHz, solvent: $CDCl_3$, standard: $CFCl_3$) δ (ppm): −79.4 to −80.1 (1F), −81.7 to −82.2 (6F), −87.2 to −88.1 (1F), −113.5 to −124.5 (12F), −130.1 (2F), −131.2 (1F), −220.0 to −223.2 (3F).

Example 2-3

Production of Compound (5b) by Hydrolysis

The product (6.3 g) obtained in Example 2-2 was charged into a 50 mL round-bottomed flask, and an ethanol solution containing 10 wt % of sodium hydroxide was dropwise added while stirring in a water bath. The temperature was slowly raised to 50° C. while continuing the stirring, and after three hours, the stirring was stopped. Extraction was carried out three times by adding R-225, and the obtained organic layer was concentrated to recover a sample of white crystals (2.3 g). As a result of the analyses by GC-MS and $^{19}$F-NMR, it was confirmed that compound (5b) was the main product.

$^{19}$F-NMR (376.2 MHz, solvent: $CDCl_3$, standard: $CFCl_3$) δ (ppm): −116.5 to −125.0 (12F), −220.0 to −224.0 (3F).

Example 3

Production of Compound (5c)

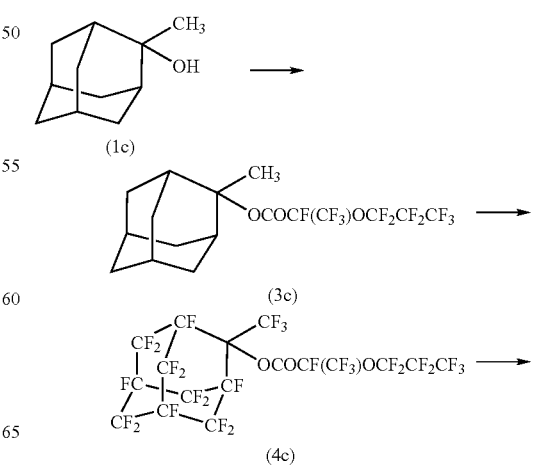

-continued

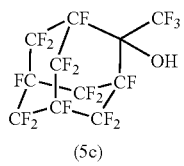

(5c)

Example 3-1

Production of Compound (3c) by Esterification Reaction 2-methyl-2-adamantanol (2.22 g, 13.4 mmol) and sodium fluoride (1.24 g, 29.5 mmol) were put into a 50 mL round-bottomed flask, and $CF_3(CF_2)_2OCF(CF_3)COF$ (5.31 g, 16.0 mmol) was dropwise added at room temperature with stirring. After completion of the dropwise addition, stirring was carried out while raising the temperature to 60° C., and while maintaining the internal temperature at from 55 to 60° C., stirring was continued for 12 hours. R-225 was added for dilution, then sodium fluoride was removed by a filter paper, followed by washing with water, whereupon magnesium sulfate was added, and the mixture was left to stand overnight. Magnesium sulfate was removed by filtration, and the filtrate was concentrated by an evaporator and then concentrated under reduced pressure by a vacuum pump to obtain 3.28 g of a crude liquid. As a result of the analyses by GC and NMR, it was confirmed that compound (3c) was formed at a selectivity of 95.9% and in a yield of 49.1%.

$^1$H-NMR (300.4 MHz, solvent: $CDCl_3$, standard: TMS) δ (ppm): 1.54 to 2.05 (m, 15H), 2.22 (s, 1H), 2.52 (s, 1H).

$^{19}$F-NMR (282.7 MHz, solvent: $CDCl_3$, standard: $CFCl_3$) δ (ppm): −79.1 to −79.8 (1F), −81.1 (3F), −81.5 (3F), −85.3 to −85.8 (1F), −129.2 (2F), −130.6 (1F).

Example 3-2

Production of Compound (4c) by Fluorination Reaction

The same autoclave as in Example 1-2 was prepared, and 20% diluted fluorine gas was blown at room temperature at a flow rate of 13.85 L/hr for one hour. Then, while blowing 20% diluted fluorine gas at the same flow rate, a solution having compound (3c) (3 g) obtained in Example 3-1 dissolved in R-113 (80 g), was injected over a period of 4.7 hours.

A reaction was carried out under the same conditions as in Example 1-2 (provided that the total amount of benzene injected was 0.22 g, and the total amount of R-113 injected was 21 mL). After the reaction, the internal pressure of the reactor was adjusted to atmospheric pressure, and nitrogen gas was blown for one hour.

The product was analyzed by $^{19}$F-NMR, whereby it was confirmed that compound (4c) was contained in a yield of 75%.

$^{19}$F-NMR (282.7 MHz, solvent: $CDCl_3$, standard: $CFCl_3$) δ (ppm): −79.4 to −80.1 (1F), −81.5 to −82.2 (9F), −87.2 to −88.1 (1F), −101.0 to −124.5 (10F), −130.1 (2F), −132.0 (1F), −215.0 to −223.6 (4F).

Example 3-3

Production of Compound (5c) by Hydrolysis

The product (3.0 g) obtained in Example 3-2 was charged into a 50 mL round-bottomed flask, and an ethanol solution containing 10 wt % of sodium hydroxide was dropwise added, while stirring in a water bath. While continuing the stirring, the temperature was slowly raised to 50° C., and after three hours, the stirring was stopped. Extraction was carried out three times by adding R-225 (mixed product of $CF_3CF_2CHCl_2/CF_2ClCF_2CHFCl$), and the obtained organic layer was concentrated to recover a sample of slightly yellow crystals (1.3 g). As a result of the analysis by GC-MS, it was confirmed that compound (5c) was formed. The selectivity was 27%.

MS: 455(M$^+$-OH), 386(M$^+$-OH—$CF_3$), 69($CF_3$).

Example 4

Production of Compound (5d)

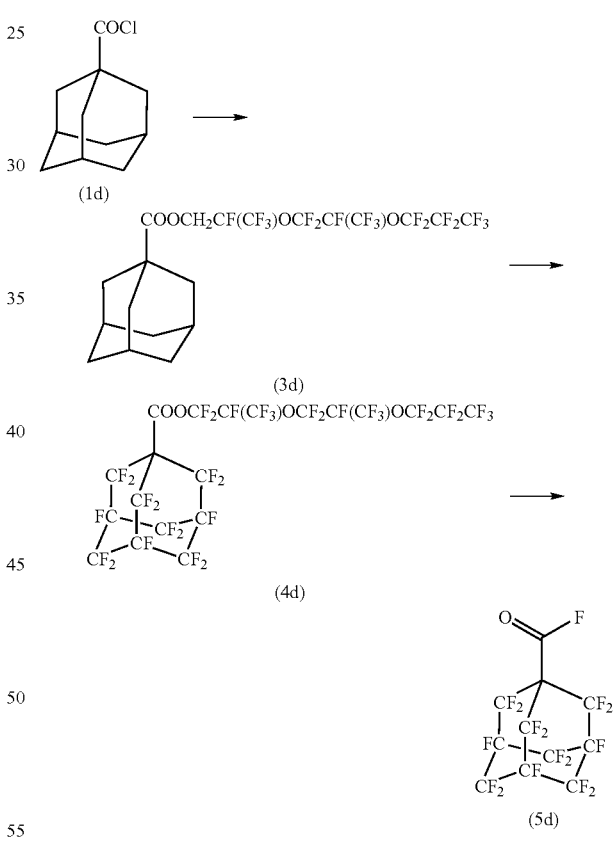

Example 4-1

Production of Compound (3d) by Esterification Reaction 1-adamantane acid chloride (1d) (1.95 g, 9.8 mmol) and pyridine (1.00 g, 12.6 mmol) were put into a 50 mL round-bottomed flask, and $CF_3(CF_2)_2OCF(CF_3)CF_2OCF(CF_3)CH_2OH$ (4.61 g, 9.6 mmol) was dropwise added at room temperature with stirring. After completion of the dropwise addition, stirring was carried out while raising the temperature to 50° C., and the stirring was continued for 5 hours while maintaining the internal temperature at from 45 to 50° C. R-225 was added for dilution, followed by washing with a dilute hydrochloric acid solution and further by washing with water, whereupon magnesium sulfate was added, and the mixture was left to stand overnight. Magnesium sulfate was removed by filtration, and the filtrate was concentrated by an evaporator to obtain 5.47 g of a crude liquid. As a result of the analyses by GC and NMR, it was confirmed that compound (3d) was formed at a selectivity of 83.8% and in a yield of 74.4%.

$^1$H-NMR (300.4 MHz, solvent: CDCl$_3$, standard: TMS) δ (ppm): 1.73 (m, 6H), 1.90 (s, 6H), 2.03 (s, 3H), 4.58 (m, 2H).

$^{19}$F-NMR (282.7 MHz, solvent: CDCl$_3$, standard: CFCl$_3$) δ (ppm): −79.8 to −80.6 (4F), −81.8 to −83.4 (9F), −130.1 (2F), −133.9 (1F), −145.5 (1F).

Example 4-2

Production of Compound (4d) by Fluorination Reaction

The same autoclave as in Example 1-2 was prepared, and after blowing 20% diluted fluorine at room temperature at a flow rate of 11.31 L/hr for 30 minutes, the internal pressure of the autoclave was raised to 0.2 MPa, and the diluted fluorine was further blown for 30 minutes.

Then, while maintaining the internal pressure of the reactor at 0.20 MPa and blowing 20% diluted fluorine gas at the same flow rate, a solution having compound (3d) (4 g) obtained in Example 4-1 dissolved in R-113 (80 g), was injected over a period of 3.3 hours.

Thereafter, a reaction was carried out in the same manner as in Example 1-2 except that the internal pressure of the autoclave was maintained at 0.20 MPa, injection of the benzene solution was repeated five times, and the total amount of benzene injected was 0.45 g, and the total amount of R-113 injected was 45 mL. After the reaction, the internal pressure of the reactor was adjusted to room temperature, and nitrogen gas was blown for one hour. The product was analyzed by $^{19}$F-NMR, whereby it was confirmed that the above-identified compound was contained in a yield of 86%.

$^{19}$F-NMR (282.7 MHz, solvent: CDCl$_3$, standard: CFCl$_3$) δ (ppm): −79.5 to −87.0 (15F), −110.5 (6F), −121.0 (6F), −130.2 (2F), −145.4 (2F), −219.1 (3F).

Example 4-3

Production of Compound (5d) by Decomposition Reaction (Liquid Phase Thermal Decomposition Reaction) of an Ester Bond Compound (4d) (4.8 g, 5.0 mmol) obtained in Example 4-2 was introduced into a 50 mL round-bottomed flask together with 0.09 g (1.5 mmol) of KF powder and heated at 140° C. for one hour in an oil bath with vigorous stirring. At the top of the flask, a reflux condenser adjusted at a temperature of 20° C., was installed, and 3.2 g of a liquid sample was recovered at a receptacle portion. As a result of the analyses by GC and $^{19}$F-NMR, it was confirmed that compound (5d) and CF$_3$(CF$_2$)$_2$OCF(CF$_3$)CF$_2$OCF(CF$_3$)COF were the main products.

$^{19}$F-NMR (376.2 MHz, solvent: CDCl$_3$, standard: CFCl$_3$) δ (ppm): 55.9 (1F), −110.2 (6F), −120.6 (6F), −219.0 (3F).

INDUSTRIAL APPLICABILITY

According to the production method of the present invention, fluorinated adamantane derivatives excellent in etching resistance and having transmittance of light with a short wavelength improved, can be produced economically advantageously from readily available materials.

The adamantane derivatives produced by the above method may be suitably used as materials for microprocessing technology which are excellent in etching resistance and have transmittance of light with a short wavelength improved, by themselves or after converted to derivatives by utilizing the reactivities of the —OH group, the =O group or the —COF group.

The entire disclosure of Japanese Patent Application No. 2002-359471 filed on Dec. 11, 2002 including specification, claims and summary is incorporated herein by reference in its entirety.

What is claimed is:

1. A compound represented by the following formula (4):

$$A^f(\text{-}G^f\text{-}Q\text{-}R^f)_n \quad (4)$$

wherein:
$A^f$ is an n-valent group (A) having n hydrogen atoms bonded to carbon atoms of adamantane converted to connecting bonds, wherein hydrogen atoms not converted to connecting bonds, may be each substituted by an alkyl group, in which at least one of hydrogen atoms forming C—H bonds is substituted by a fluorine atom,
$R^f$: is an fluorinated monovalent organic group having at least two carbon atoms or a $C_{2\text{-}20}$ perfluoroalkyl group or a $C_{2\text{-}20}$ perfluoroalkyl group containing an etheric oxygen atom,
n is an integer of from 1 to 4,
$G^f$ is —CF$_2$— or a single bond, and
Q is —C(=O)O— or —O—C(=O)—.

2. The compound according to claim 1, wherein Q is —C(=O)O—.

3. A compound selected from compounds represented by the following formulae:

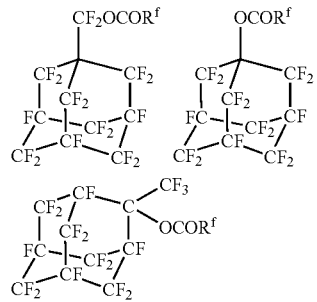

wherein $R^f$ is a perfluorinated monovalent organic group containing an etheric oxygen atom.

4. The compound according to claim 3, wherein $R^f$ is a $C_{2\text{-}20}$ perfluoroalkyl group containing an etheric oxygen atom.

5. The compound according to claim 1, wherein $R^f$ is a fluorinated monovalent organic group having at least two carbon atoms.

6. The compound according to claim 1, wherein $R^f$ is $C_{2\text{-}20}$ perfluoroalkyl group containing an etheric oxygen atom.

7. The compound according to claim 1, wherein $R^f$ is —$CF(CF_3)OCF_2CF_2CF_3$.

8. The compound according to claim 3, wherein $R^f$ is —$CF(CF_3)OCF_2CF_2CF_3$.

9. The compound according to claim 1, wherein Q is —C(=O)O— or O—C(=O)—.

10. The compound according to claim 1, wherein $G^f$ is —$CF_2$—.

11. The compound according to claim 1, wherein G is a single bond.

* * * * *